United States Patent
Lee et al.

(10) Patent No.: US 11,638,741 B2
(45) Date of Patent: May 2, 2023

(54) COMPOSITION FOR TREATING CANCER OR INHIBITING CANCER METASTASIS, INCLUDING TFG OR TFMG NANOPARTICLES

(71) Applicant: KYUNGPOOK NATIONAL UNIVERSITY INDUSTRY-ACADEMIC COOPERATION FOUNDATION, Daegu (KR)

(72) Inventors: You-Mie Lee, Daegu (KR); Jong-Sup Bae, Daegu (KR)

(73) Assignee: KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 55 days.

(21) Appl. No.: 16/688,128

(22) Filed: Nov. 19, 2019

(65) Prior Publication Data

US 2020/0155644 A1    May 21, 2020

(51) Int. Cl.
*A61K 38/17*  (2006.01)
*A61P 35/04*  (2006.01)
*A61K 9/51*   (2006.01)

(52) U.S. Cl.
CPC .............. *A61K 38/17* (2013.01); *A61K 9/51* (2013.01); *A61P 35/04* (2018.01)

(58) Field of Classification Search
None
See application file for complete search history.

(56) References Cited

U.S. PATENT DOCUMENTS

| | | | | |
|---|---|---|---|---|
| 10,513,545 B2 * | 12/2019 | Bae | ........ | A61K 38/16 |
| 2002/0107204 A1 * | 8/2002 | D'Andrea | ........ | C07K 5/06191 |
| | | | | 548/306.4 |
| 2005/0232925 A1 * | 10/2005 | Sukhatme | ........ | A61K 2300/00 |
| | | | | 424/155.1 |
| 2019/0016764 A1 * | 1/2019 | Bae | ........ | C07K 14/47 |

FOREIGN PATENT DOCUMENTS

KR    1020050060175 A    6/2005
WO    WO 2017/039383    *    3/2017

OTHER PUBLICATIONS

Anton et al. ('Receptor of activated protein c promotes metastasis and correlates with clinical outcome in lung adenocarcinoma' American Journal of Respiratory and Critical Care Medicine v186(1) 2012 pp. 96-105) (Year: 2012).*
Choi et al. ('Abstract 2132:Anti-vascular inflammatory nanoparticles inhibit tumor progression and metastasis through vascular normalization' Proceedings of the American Association for Cancer Research Annual Meeting; published Jul. 2018 pp. 1-4) (Year: 2018).*
Dasari et al. ('Cisplatin in cancer therapy: molecular mechanisms of action' European J Pharmacol 2014 printed as pp. 1-33) (Year: 2014).*
Lee et al. ('A double chambered protein nanocage loaded with thrombin receptor agonist peptide (TRAP) and gamma-carboxyglutamic acid of protein C (PC-Gla) for sepsis treatment' Advanced Materials v27 2015 pp. 6637-6643) (Year: 2015).*
Kamath et al. ('Signaling from protease-activated receptor-1 inhibits migration and invasion of breast cancer cells' Cancer Research v61 Aug. 1, 2001 pp. 5933-5940) (Year: 2001).*
Wang et al. ('Knockdown of EPCR inhibits the proliferation and migration of human gastric cancer cells via the ERK1/2 pathway in a PAR-1-dependent manner' Oncology Reports v39 Apr. 2018 pp. 1843-1852) (Year: 2018).*

* cited by examiner

*Primary Examiner* — Ronald T Niebauer

(74) *Attorney, Agent, or Firm* — Riverside Law LLP

(57) ABSTRACT

The present invention relates to a composition for preventing or treating cancer, a composition for inhibiting the metastasis of cancer, and the like, including TFG nanoparticles or TFMG nanoparticles, and more particularly, to a composition exhibiting effects of treating cancer, effects of inhibiting the metastasis of cancer, and the like by normalizing blood vessels inside a tumor.

8 Claims, 9 Drawing Sheets
Specification includes a Sequence Listing.

COMPOSITION FOR TREATING CANCER OR INHIBITING CANCER METASTASIS, INCLUDING TFG OR TFMG NANOPARTICLES

CROSS-REFERENCE TO RELATED APPLICATION

This application claims priority to and the benefit of Korean Patent Application No. 10-2018-0143010, filed on Nov. 19, 2018, the disclosure of which is incorporated herein by reference in its entirety.

BACKGROUND

1. Field of the Invention

The present invention relates to a composition for treating cancer or inhibiting cancer metastasis, including TFG or TFMG nanoparticles.

2. Discussion of Related Art

Since malignant progressive tumor cells proliferate faster than endothelial cells that form blood vessels, the newly formed blood vessels are not normally distributed inside cancer tissues, and thus blood is not sufficiently supplied, and as a result, the deficiency of nutrients, acidification, and oxygen deficiency are induced. The median value of oxygen partial pressure in normal tissues is substantially 40 to 60 mmHg, and in the case of solid cancer, the median value of oxygen partial pressure is 10 mmHg or less in most cases. Cancer cells are adapted to such hypoxic conditions, and it is known that cancer cells become even more malignant under hypoxic conditions and are resistant to various cancer treatment therapies such as anticancer drug therapy and radiation therapy.

Therefore, when abnormal blood vessels inside cancer tissues can be normalized, it is expected to be possible not only to effectively suppress proliferation, metastasis, and the like of cancer cells, but also to effectively enhance the treatment efficiency of existing cancer treatment therapies.

PRIOR ART DOCUMENT

Patent Document

Korean Patent Application Laid-Open No. 10-2005-0060175

SUMMARY OF THE INVENTION

The present invention has been devised in order to solve the aforementioned problems in the related art, and an object thereof is to provide a composition for preventing or treating cancer, a composition for inhibiting cancer metastasis, a method for preventing or treating cancer, a method for inhibiting the metastasis of cancer, and the like, including TFG nanoparticles or TFMG nanoparticles capable of normalizing blood vessels inside cancer tissues as an active ingredient by alleviating hypoxic conditions inside cancer tissues, and simultaneously promoting the proliferation of endothelial cells.

However, the technical problems which the present invention intends to solve are not limited to the technical problems which have been mentioned above, and other technical problems which have not been mentioned will be apparently understood by a person with ordinary skill in the art to which the present invention pertains from the following description.

The present invention provides a pharmaceutical composition for preventing or treating cancer, including, as an active ingredient, nanoparticles including an amino acid sequence represented by SEQ ID NO: 1 or nanoparticles including an amino acid sequence represented by SEQ ID NO: 2.

Further, the present invention provides an adjuvant of an anticancer therapy, including, as an active ingredient, nanoparticles including an amino acid sequence represented by SEQ ID NO: 1 or nanoparticles including an amino acid sequence represented by SEQ ID NO: 2.

In addition, the present invention provides a pharmaceutical composition for preventing or treating cancer, including: an anticancer agent; and, as an active ingredient, nanoparticles including an amino acid sequence represented by SEQ ID NO: 1 or nanoparticles including an amino acid sequence represented by SEQ ID NO: 2.

Furthermore, the present invention provides a pharmaceutical composition for inhibiting cancer metastasis, including, as an active ingredient, nanoparticles including an amino acid sequence represented by SEQ ID NO: 1 or nanoparticles including an amino acid sequence represented by SEQ ID NO: 2.

Further, the present invention provides a method for preventing or treating cancer, including a step of administering, to an individual, a composition including, as an active ingredient, nanoparticles including an amino acid sequence represented by SEQ ID NO: 1 or nanoparticles including an amino acid sequence represented by SEQ ID NO: 2. The method may further include a step of performing an anticancer therapy.

In addition, the present invention provides a method for inhibiting the metastasis of cancer, including a step of administering, to an individual, a composition including, as an active ingredient, nanoparticles including an amino acid sequence represented by SEQ ID NO: 1 or nanoparticles including an amino acid sequence represented by SEQ ID NO: 2.

Furthermore, the present invention provides a method for preventing or treating cancer, including a step of administering, to an individual, a composition including an anticancer agent, and, as an active ingredient, nanoparticles including an amino acid sequence represented by SEQ ID NO: 1 or nanoparticles including an amino acid sequence represented by SEQ ID NO: 2. That is, the present invention provides a method for preventing or treating cancer by administering an anticancer agent and nanoparticles in combination.

In an embodiment of the present invention, the nanoparticles are a polypeptide represented by SEQ ID NO: 1 or SEQ ID NO: 2, and functional equivalents of the polypeptide, which are polypeptides that have, as a result of addition, substitution, or deletion of an amino acid, at least 60%, preferably at least 70%, more preferably at least 80%, and even more preferably at least 90% sequence homology with the amino acid sequence, and exhibit substantially the same activity as the polypeptide, are also included in the scope of rights of the present invention.

In another embodiment of the present invention, the individual is a patient with cancer or patient undergoing anticancer therapy.

In still another embodiment of the present invention, the nanoparticles normalize blood vessels inside cancer tissues, and the normalization is not limited thereto as long as it is a form that may alleviate hypoxic conditions inside cancer tissues, promote the proliferation of endothelial cells, or normalize abnormal blood vessels inside cancer tissues. Further, the composition or adjuvant may be used to improve treatment effects of anticancer therapy by normalizing blood vessels inside cancer tissues. The anticancer therapy is not limited thereto as long as it is preferably therapy that is used as radiation therapy, surgical therapy, anticancer agent therapy, and the like, or a method for treating cancer. The type of anticancer agent is not particularly limited, and may include not only publicly known anticancer agents used for the treatment of cancer, but also novel anticancer agents to be investigated in the future, and examples thereof include cisplatin, tamoxifen, toremifene, fulvestrant, diindolylmethane, exemestane, raloxifene, an aromatase inhibitor, doxorubicin, oxaliplatin, vincristine, gemcitabine, 5-FU, anthracycline, taxane, irinotecan, paclitaxel, eribulin, docetaxel, and the like, but are not limited thereto.

In yet another embodiment of the present invention, the composition or adjuvant inhibits the proliferation, metastasis, recurrence, and the like of cancer, or inhibits resistance to anticancer therapy, but is not limited thereto as long as it is a generally used kind of method for treating cancer.

In still yet another embodiment of the present invention, the cancer is breast cancer, lung cancer, glioma cancer, colorectal cancer, uterine cancer, ovarian cancer, prostate cancer, gastric cancer, a brain tumor, multiple myeloma, pediatric cancer, rectal cancer, colon cancer, thyroid cancer, oral cancer, pharyngeal cancer, laryngeal cancer, bladder cancer, renal cancer, liver cancer, pancreatic cancer, bone cancer, skin cancer, and the like, but is not limited thereto as long as it is a type of cancer whose symptoms may be aggravated by the abnormalization of blood vessels inside a tumor.

In a further embodiment of the present invention, the metastasis is metastasis into the lungs or the lymph nodes.

Further, the present invention provides a use of a composition including, as an active ingredient, nanoparticles including an amino acid sequence represented by SEQ ID NO: 1 or nanoparticles including an amino acid sequence represented by SEQ ID NO: 2, for inhibiting cancer metastasis.

Advantageous Effects

According to the present invention, TFG nanoparticles or TFMG nanoparticles normalize blood vessels in cancer tissues through attenuating hypoxic condition and promoting endothelial blood vessel production. Therefore, it is expected that it can be effectively used for various cancer treatments because it can not only suppress the proliferation, metastasis, and recurrence of cancer cells but also significantly increase the treatment efficiency of various cancer treatment therapies that are be used. In addition, it is expected to be used as a therapeutic adjuvant for disease with abnormal blood vessels due to vascular hyperplasia.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
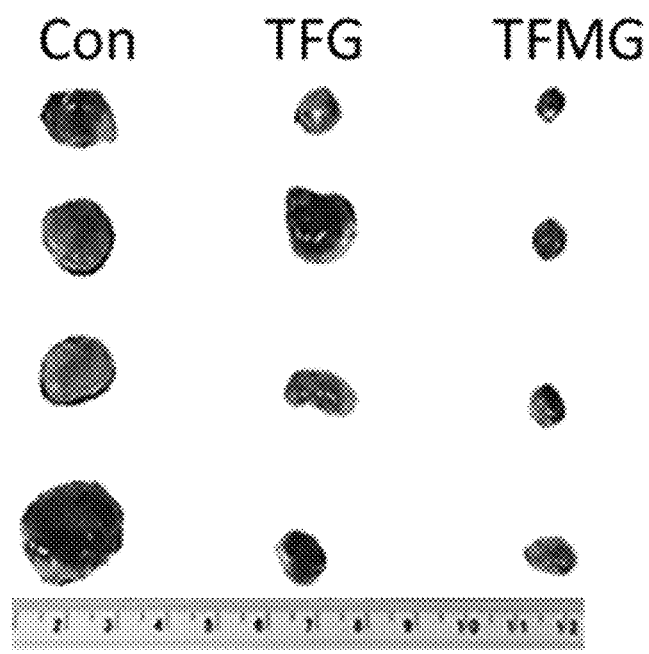
FIG. 1 is a view illustrating the results confirming the effects of the TFG nanoparticles or TFMG nanoparticles according to an example of the present invention on the inhibition of the proliferation of a tumor.

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

In the present invention, it was confirmed that TFG nanoparticles or TFMG nanoparticles can inhibit the proliferation, metastasis, recurrence, resistance, and the like of cancer cells and improve the treatment effects of anticancer therapy that is conventionally used by alleviating hypoxic conditions inside cancer tissues and promoting the proliferation of blood vessel endothelial cells to normalize the blood vessels in cancer tissues. Therefore, it is expected that the TFG nanoparticles or TFMG nanoparticles of the present invention can also be used alone for the purpose of preventing or treating cancer, and can be used in combination with existing anticancer therapy to significantly improve cancer treatment effects.

As used herein, a "nanoparticle" is a nano-sized polypeptide particle, and is preferably a polypeptide including an amino acid sequence represented by SEQ ID NO: 1 or a polypeptide including an amino acid sequence represented by SEQ ID NO: 2.

As used herein, "adjuvant" refers to an auxiliary drug that is used for the purpose of improving and/or enhancing the treatment effects by assisting the medicinal effect of a main drug, that is, an anticancer agent, improving and/or enhancing the treatment effects by inhibiting resistance to the main drug, or blocking or alleviating a harmful action of the main drug, and the adjuvant of the present invention is not limited as long as it includes TFG nanoparticles or TFMG nanoparticles as an active ingredient.

As used herein, "prevention" refers to all actions that inhibit a disorder such as cancer or delay the onset of the disorder with administration of the composition according to the present invention.

As used herein, "treatment" refers to all actions in which symptoms such as cancer are ameliorated or advantageously changed with administration of the composition according to the present invention.

As used herein, "individual" refers to a subject to which the composition of the present invention may be administered, and the subject is not limited.

As used herein, a "pharmaceutical composition" may be in the form of a capsule, a tablet, granules, an injection, an ointment, a powder, or a beverage, and the pharmaceutical composition may target humans. The pharmaceutical composition is not limited thereto, but may be individually formulated into the form of an oral dosage form such as a powder, granules, a capsule, a tablet, or an aqueous suspension, an external preparation, a suppository, and a sterile injectable solution. The pharmaceutical composition of the present invention may include a pharmaceutically acceptable carrier. As the pharmaceutically acceptable carrier, a binder, a lubricant, a disintegrant, an excipient, a solubilizing agent, a dispersing agent, a stabilizer, a suspending agent, a colorant, a perfume, and the like may be used when orally administered, an injection may be used in a mixture with a buffering agent, a preservative, an analgesic, a solubilizer, an isotonic agent, a stabilizer, and the like, and in the case of topical administration, a base, an excipient, lubricant, a preservative, and the like may be used. The formulation of the pharmaceutical composition of the present invention may be variously prepared by mixing the pharmaceutical composition of the present invention with the pharmaceutically acceptable carrier as described above. For example, the formulation may be prepared in the form of a tablet, a troche, a capsule, an elixir, a suspension, a syrup, a wafer, and the like when orally administered, and in the case of an injection, the injection may be formulated into unit dosage ampoules or in multiple dosage forms. The pharmaceutical composition of the present invention may be formulated into other solutions, suspensions, tablets, capsules, or sustained-release preparations.

Meanwhile, as an example of suitable carriers, excipients and diluents for formulation, it is possible to use lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate or mineral oil. Further, the pharmaceutical composition of the present invention may further include a filler, an anticoagulant, a lubricant, a wetting agent, a flavoring agent, an emulsifying agent, an antiseptic, and the like.

The route of administration of the pharmaceutical composition according to the present invention includes, but is not limited to, oral, intravenous, intramuscular, intraarterial, intramedullary, intrathecal, intracardiac, transdermal, subcutaneous, intraperitoneal, intranasal, intestinal canal, topical, sublingual or rectal. Oral or parenteral administration is preferred. As used herein, the term "parenteral" includes subcutaneous, intradermal, intravenous, intramuscular, intraarticular, intrasynovial, intrasternal, intrathecal, intralesional and intracranial injection or infusion techniques. The pharmaceutical composition of the present invention may also be administered in the form of a suppository for rectal administration.

The pharmaceutical composition of the present invention varies depending on various factors including the activity of the specific compound used, age, body weight, general health, sex, diet, time of administration, route of administration, rate of excretion, drug combination and the severity of the particular disease to be prevented or treated, and the dosage of the pharmaceutical composition varies depending on the condition of the patient, the body weight, the degree of the disease, the form of the drug, the route of administration and the period of time, but may be appropriately selected by a person skilled in the art, and may be 0.0001 to 50 mg/kg or 0.001 to 50 mg/kg daily. The administration may be carried out once daily, or may be divided into several times. The dosage is not intended to limit the scope of the present invention in any way. The pharmaceutical composition according to the present invention may be formulated into pills, liquids, capsules, solutions, gels, syrups, slurries, and suspensions.

Hereinafter, preferred examples for helping with understanding of the present invention will be suggested. However, the following examples are provided only so that the present invention can be more easily understood, and the contents of the present invention are not limited by the following examples.

EXAMPLES

Example 1: Purification of TFG Nanoparticles or TFMG Nanoparticles

In order to purify TFG nanoparticles (a TRAP-ferritin monomer fragment-PC-Gla fusion polypeptide; a polypeptide represented by SEQ ID NO: 1) or TFMG nanoparticles (a TRAP-ferritin monomer fragment-linker-PC-Gla fusion polypeptide; a polypeptide represented by SEQ ID NO: 2), TFG plasmids and TFMG plasmids were constructed in the same manner as the method in "Korean Patent Application Laid-Open No. 10-2015-0124472." Then, *Escherichia coli*

BL21 (DE3) expression strain was transformed using each prepared plasmid. Then, the transformed *E. coli* was shaking-cultured at 37° C. in a Luria Bertani (LB) medium supplemented with 30 μg/mL of kanamycin until OD600 nm=0.5. Thereafter, the expression of the nanoparticles was induced by treating the *E. coli* with 0.1 M isopropyl-β-D-1-thiogalactopyranoside (IPTG) and additionally culturing the *E. coli* for 5 hours. The *E. coli* where the expression of the nanoparticles was induced was isolated using centrifugation to remove the supernatant, and the *E. coli* from which the supernatant was removed was stored at −80° C. Then, in order to isolate the nanoparticles, the stored *E. coli* was thawed from ice, and then the *E. coli* was suspended using a lysis buffer (20 mM Tris-HCl pH 8.0, 100 mM NaCl, 1% Triton X-100, 1 mM phenylmethane sulfonyl fluoride (PMSF), 1 mM dithiothreitol (DTT), and 1:1000 dilution protease inhibitor cocktail (Sigma)), and the nanoparticles were extracted from the cells using an ultrasonic homogenizer to lysate the *E. coli*. The inclusion body that had not been extracted from the cells was treated with a binding buffer (20 mM Tris-HCl pH 8.0, 300 mM NaCl, and 10 mM imidazole) including 8 M urea, reacted at room temperature for 1 hour, and lysated. Then, in order to purify the nanoparticles, affinity chromatography using a nickel ion column was used, and the nanoparticles were washed using a buffer (20 mM Tris HCL, pH 8.0, 500 mM NaCl, and 30 mM imidazole) including 8 M urea. Then, after the fusion polypeptide bound to the column was eluted using an elusion buffer (20 mM Tris-HCl pH 8.0, 100 mM NaCl, and 300 mM imidazole), the fusion polypeptide was reactivated by a stepwise dialysis method of urea.

Example 2: Confirmation of Effects of TFG Nanoparticles or TFMG Nanoparticles on Treatment of Tumor 2.1. Confirmation of Effects of TFG Nanoparticles or TFMG Nanoparticles on Inhibition of Proliferation of Tumor In order to confirm the effects of the TFG nanoparticles or TFMG nanoparticles on the proliferation of cancer cells, after a tumor animal model was prepared by allografting 2 to $5 \times 10^5$ cells of Lewis lung carcinoma (LLC) as a murine lung cancer cell line into 6- to 7-week-old C57BL/6J mice, 100 nM of the TFG nanoparticles or TFMG nanoparticles was injected into the tail vein on days 7, 10, and 13, and then the size and survival proportion of the tumor were observed by obtaining the tumor on day 14. The tumor size was measured by substitution into the formula "$0.5 \times A \times B^2$ (A: diameter in the longest direction, and B: diameter in a direction vertical to the longest direction)." An equal amount of phosphate buffered saline was administered to a control (Con). Animal care and all experimental procedures were performed in accordance with the laws and regulations for animal experiments. In order to show a significant difference between the corresponding groups in at least 3 of all the experimental result values, an ANOVA verification was performed, and only values with statistical significance of P-values <0.05 were shown as the average value±standard deviations (SD). The results are illustrated in FIGS. 1 to 3.

Figure 2:
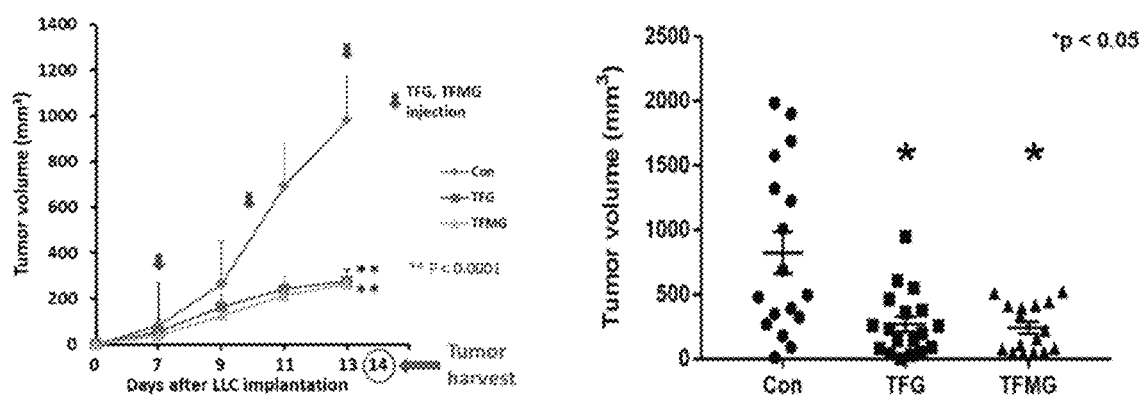
FIG. 2 is a view illustrating the results quantifying the ability of the TFG nanoparticles or TFMG nanoparticles according to an example of the present invention to inhibit the proliferation of a tumor.

As illustrated in FIGS. 1 and 2, it was confirmed that, compared with the control, the experimental group to which the TFG nanoparticles had been administered exhibited a tumor growth inhibition effect of 28.2%, the experimental group to which the TFMG nanoparticles had been administered exhibited a tumor growth inhibition effect of 27.0%, showing that the growth of tumor was remarkably inhibited.

Figure 3:
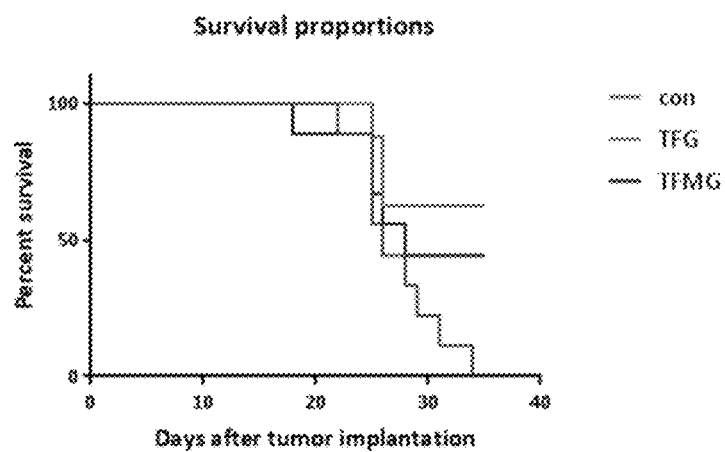
FIG. 3 is a view illustrating the results confirming the effects of the TFG nanoparticles or TFMG nanoparticles according to an example of the present invention on the enhancement of the survival proportion.

Further, as illustrated in FIG. 3, it was confirmed that, when the TFG nanoparticles or TFMG nanoparticles were administered, the survival proportion also increased.

From the results, it could be confirmed that the TFG nanoparticles or TFMG nanoparticles exhibited effects of inhibiting the growth of tumors.

2.2. Confirmation of Effects of TFG Nanoparticles or TFMG Nanoparticles on Inhibition of Metastasis of Tumor In order to confirm whether the TFG nanoparticles or TFMG nanoparticles affected the inhibition of metastasis of tumor, a tumor animal model was prepared in the same manner as in Example 2.1, and then the TFG nanoparticles or TFMG nanoparticles were injected. Then, a tumor removal surgery was performed on day 14, and it was confirmed whether the tumor metastasized into the lungs and the inguinal lymph nodes (LNs) on day 28. The metastasis into the inguinal lymph nodes was confirmed using immunohistochemistry (IHC) analyses. More specifically, the lymph nodes obtained to confirm cytokeratin positive tumor cells were fixed with 3.7% paraformaldehyde (PFA), and then dehydrated by treatment with a 10 to 40% sucrose solution at each step. Then, after the permeability of cells was increased by treatment with 0.3% Triton X-100 and a blocking process was performed using a bovine serum albumin (BSA), the lymph nodes were treated with rat anti-CD31 (BD Biosciences), mouse anti-α-SMA (Abcam), mouse anti-pimonidazole (HPI), mouse anti-cytokeratin II (Millipore), or rabbit anti-LYVE-1 (Angiobio) antibodies, and reacted at 4° C. for 16 hours. Then, unbound antibodies were washed using phosphate buffered saline, and then treated with Alexa Fluor 488-, 568-, or 647-conjugated anti-mouse IgG (Invitrogen), Alexa Fluor 594- or 647-conjugated anti-rat IgG (Invitrogen), Alexa Fluor 488-, 568-, or 647-conjugated anti-rabbit IgG (Invitrogen) antibodies that were secondary antibodies to a fluorescent marker, and reacted at room temperature for 1 hour. Then, finally, cellular nuclei were stained by treatment with Hoechst33258 (Invitrogen) for 1 minute, and then observed using a confocal microscope, and a fluorescence value was quantified using ImageJ. In order to show a significant difference between the corresponding groups in at least 3 of all the experimental result values, an ANOVA verification was performed, and only values with statistical significance of P-values <0.05 were shown as the average value±standard deviations (SD). The results are illustrated in FIGS. 4 to 5.

Figure 4:
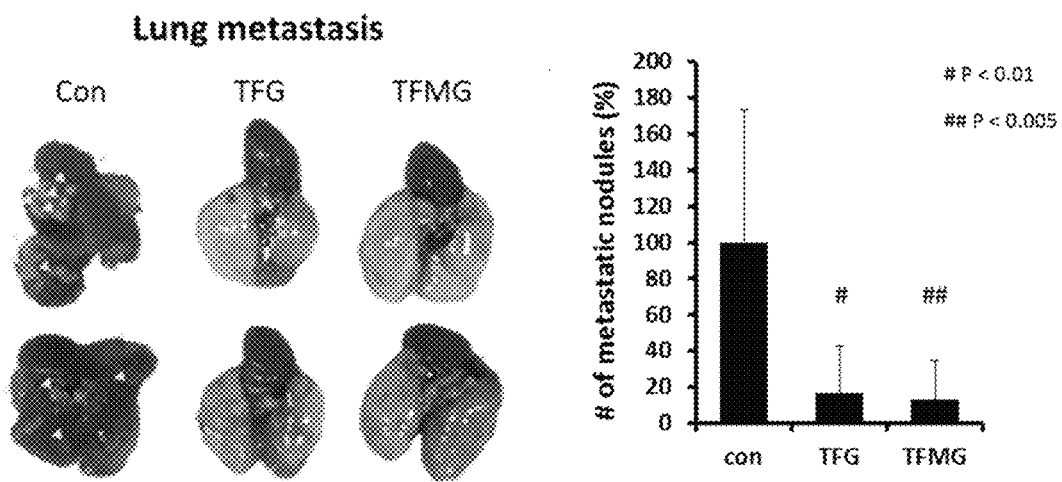
FIG. 4 is a view illustrating the results confirming the effects of the TFG nanoparticles or TFMG nanoparticles according to an example of the present invention on the inhibition of lung metastasis.

As illustrated in FIG. 4, it was confirmed that, compared with the control, the metastasis of the tumor into the lungs was inhibited by 83.4% when the TFG nanoparticles were administered, and the metastasis of the tumor into the lungs was inhibited by 86.4% when the TFMG nanoparticles were administered.

Figure 5:
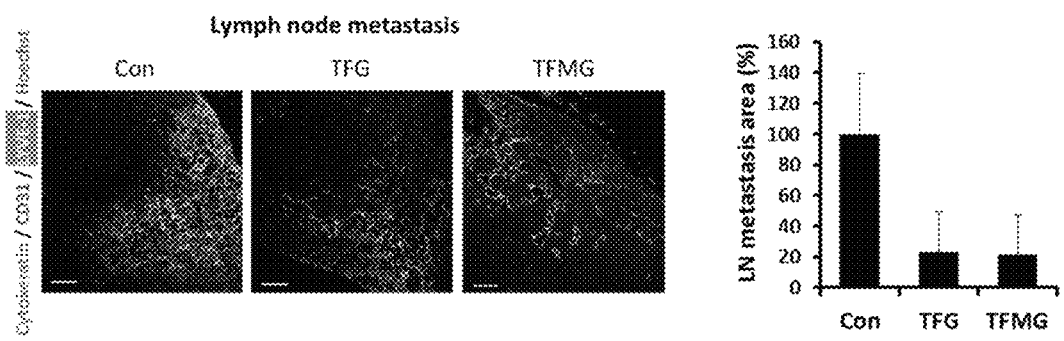
FIG. 5 is a view illustrating the results confirming the effects of the TFG nanoparticles or TFMG nanoparticles according to an example of the present invention on the inhibition of the lymph node metastasis.

In addition, as illustrated in FIG. 5, as compared with the control, a lymph node metastasis inhibition rate of 76.9% was exhibited when the TFG nanoparticles were administered, and a lymph node metastasis inhibition rate of 78.1% was exhibited when the TFMG nanoparticles were administered.

From the results, it could be confirmed that the TFG nanoparticles or TFMG nanoparticles exhibited effects of inhibiting the metastasis of tumors.

Example 3: Confirmation of Effects of TFG Nanoparticles or TFMG Nanoparticles on Blood Vessels in Tumor The structure and function of blood vessels in a tumor were analyzed using the tumor obtained in the same manner as in Example 2.1. More specifically, the obtained tumor was observed using a confocal microscope after fluorescent staining was performed through IHC analyses in the same manner as in Example 2.2. In order to measure the hypoxic state inside the tumor, 60 mg/kg of Hypoxyprobe-1™ (pimonidazole hydrochloride; PIMO, HPI) was administered through intraperitoneal injection, and 90 minutes later, the mouse was sacrificed and the tumor extracted. The extracted tumor was incised, and then stained with mouse anti-hypoxyprobe antibody (HPI), Alexa Fluor 488-, 568-, or 647-conjugated anti-mouse IgG (Invitrogen), and in order to measure the degree of leakage of blood vessels in the tumor, 40 mg/kg of Hoechst33258 (Invitrogen) was intravenously injected 5 minutes before the mouse was sacrificed. The prepared sample was obtained using a confocal microscope. The results are illustrated in FIGS. 6 and 7.

Figure 6:
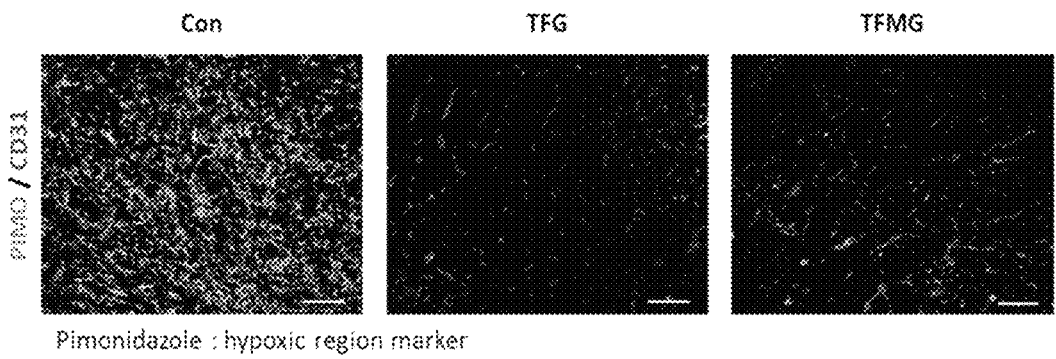
FIG. 6 is a view illustrating the results confirming the effects of the TFG nanoparticles or TFMG nanoparticles according to an example of the present invention on the alleviation of hypoxic conditions inside cancer tissues.

As illustrated in FIG. 6, as a result of staining the inside of the tumor with pimonidazole (PIMO) as a hypoxia marker, it was confirmed that the hypoxic state generally observed inside cancer was remarkably decreased in the experimental group to which the nanoparticles had been administered.

Figure 7:
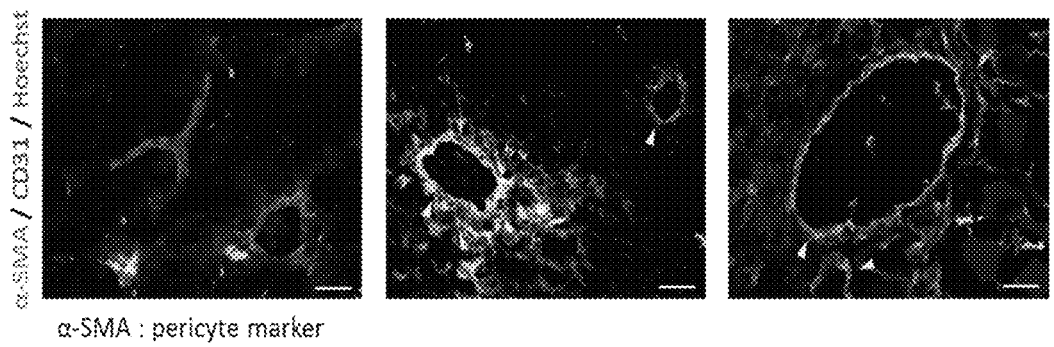
FIG. 7 is a view illustrating the results confirming the effects of the TFG nanoparticles or TFMG nanoparticles according to an example of the present invention on the promotion of blood vessel endothelial cells inside cancer tissues.

Further, as illustrated in FIG. 7, it was confirmed that blood vessels covered with α-smooth muscle actin positive pericytes were increased in the tumor of the mouse to which the TFG nanoparticles or TFMG nanoparticles had been administered.

From the results, it could be confirmed that the TFG nanoparticles or TFMG nanoparticles normalize abnormal blood vessels in a tumor, and through this, it could be also confirmed that the TFG nanoparticles or TFMG nanoparticles could inhibit the proliferation and metastasis of a tumor by normalizing abnormal blood vessels in the tumor.

Example 4: Confirmation of Effects of TFG Nanoparticles or TFMG Nanoparticles on Enhancement of Anticancer Agent Treatment Effects 4.1. Confirmation of Effects of Inhibiting Proliferation of Tumor In order to confirm whether the treatment effects of a conventionally used anticancer agent may be enhanced by normalizing abnormal blood vessels in a tumor, 100 nM of the TFG nanoparticles or TFMG nanoparticles was injected into the tail vein in a tumor animal model prepared in the same manner as in Example 2.1 on days 7, 10, and 13, cisplatin was injected at a concentration of 3 mg/kg on days 7 and 12, and the survival proportion was measured. An equal amount of phosphate buffered saline was injected into a negative control (Con), and an equal amount of cisplatin was injected alone into a positive control (Cis). Then, the tumor size was confirmed by obtaining tumors on days 9, 11, and 13. The results are illustrated in FIGS. 8 and 9.

Figure 8:
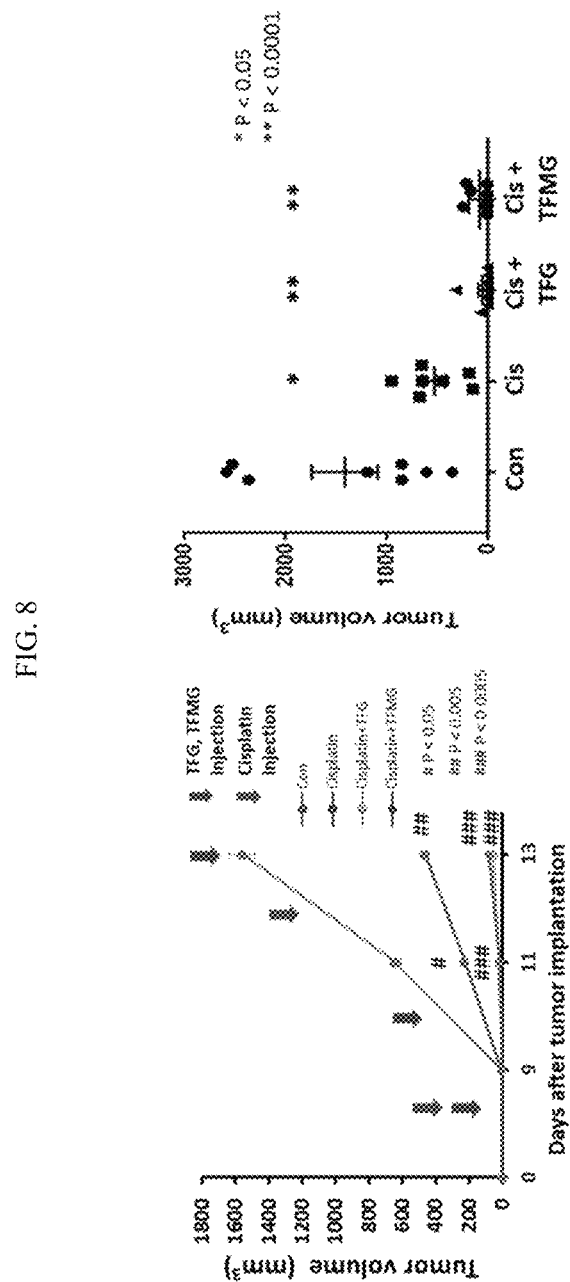
FIG. 8 is a view illustrating the results confirming the effects of the TFG nanoparticles or TFMG nanoparticles according to an example of the present invention on the enhancement of inhibiting the proliferation of a tumor of an anticancer agent.

As illustrated in FIG. 8, even in the case of the positive control to which cisplatin was administered alone, the growth of the tumor was inhibited by 62.6%, but in the case of the experimental group to which the TFG nanoparticles or TFMG nanoparticles were administered together, it was confirmed that effects of inhibiting the growth of the tumor by 96.2% and 94.3%, respectively, were exhibited on day 13.

Figure 9:
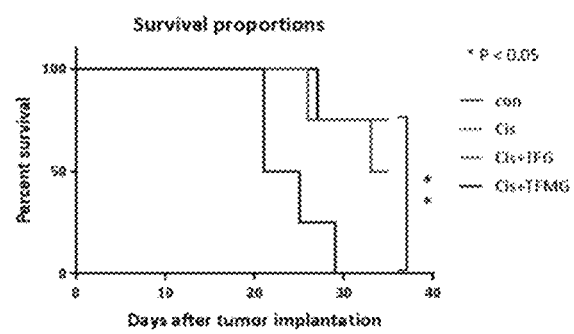
FIG. 9 is a view illustrating the results confirming the effects of the TFG nanoparticles or TFMG nanoparticles according to an example of the present invention on the enhancement of cancer treatment effects of an anticancer agent as the survival proportion.

In addition, as illustrated in FIG. 9, it was confirmed that, in the case of the experimental group to which cisplatin and the nanoparticles were administered together, the survival proportion was significantly prolonged as compared to the control.

From the results, it could be confirmed that the TFG nanoparticles or TFMG nanoparticles could enhance the treatment efficacy effects of the anticancer agent.

4.2. Confirmation of Normalization Effects of Blood Vessels

When the TFG nanoparticles or TFMG nanoparticles were administered together with cisplatin, an experiment was performed in the same manner as in Example 3 in order to confirm the effects of the combination administration on the blood vessel normalization. The results are illustrated in FIG. 10.

Figure 10:
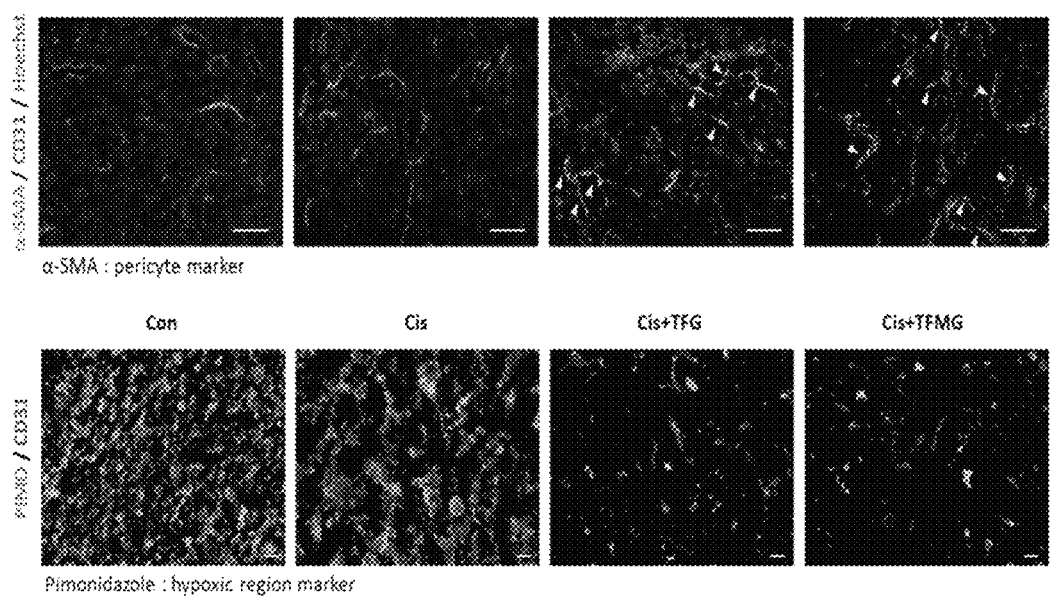
FIG. 10 is a view illustrating the results confirming the normalization effects of blood vessels inside cancer tissues when the TFG nanoparticles or TFMG nanoparticles according to an example of the present invention are administered in combination with an anticancer agent.

As illustrated in FIG. 10, it was confirmed that the hypoxic state inside the tumor was decreased and smooth muscle actin positive pericytes were produced only in the experimental group to which cisplatin and the nanoparticles were administered together. From the results, it could be confirmed that the existing anticancer agent failed to affect the normalization of blood vessels inside the tumor, but when the nanoparticles were also administered, blood vessels were normalized by the nanoparticles, and accordingly, the treatment effects caused by the anticancer agent could be enhanced.

Example 5: Confirmation of Anticancer Effects in Naturally Occurring Tumor Model 5.1. Confirmation of Effects of Inhibiting Proliferation of Tumor In order to confirm whether the same effects were also exhibited in a naturally occurring tumor model, an experiment was performed using MMTV-PyMT gene transplanted mice. More specifically, the sizes of all the distinct nodules of 12-week-old mice were measured, and the mice were grouped according to the sizes of the tumors. Then, 100 nM of the TFG nanoparticles or TFMG nanoparticles was injected into their tail veins, and the tumors were obtained when the mice became 15 weeks old. Then, the sizes of the tumors were measured in the same manner as in Example 2.1. The results are illustrated in FIG. 11.

Figure 11:
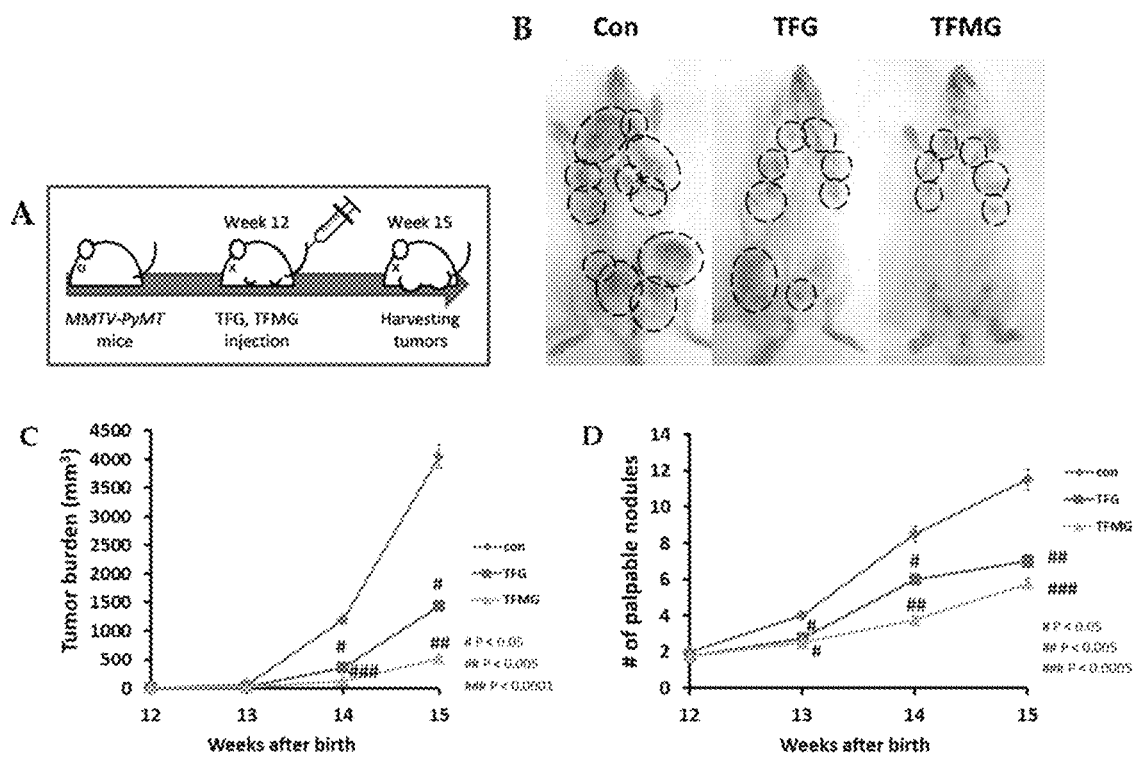
FIG. 11 is a view illustrating the results confirming the effects of the TFG nanoparticles or TFMG nanoparticles according to an example of the present invention on the inhibition of the proliferation of a tumor in a naturally occurring tumor model.

As illustrated in FIG. 11, it was confirmed that, in the experimental group to which the TFG nanoparticles were administered, the sizes of the tumors were decreased by 85%, and in the experimental group to which the TFMG nanoparticles were administered, the sizes of the tumors were decreased by 87.2%. Furthermore, it was confirmed that the number of nodules with tumors was also decreased by 39.1% and 59%, respectively. From the results, it could be confirmed that the TFG nanoparticles or TFMG nanoparticles also exhibited effects of inhibiting the proliferation of a tumor in the naturally occurring tumor model.

5.2. Confirmation of Effects of Inhibiting Metastasis of Tumor

In order to confirm whether effects of inhibiting the metastasis of tumor are also exhibited in the naturally occurring tumor model, it was confirmed that 100 nM of the TFG nanoparticles or TFMG nanoparticles was injected into the tail veins of 12-week-old MMTV-PyMT gene transplanted mice, and the metastasis inhibition rate was confirmed in the same manner as in Example 2.2 when the mice became 15 weeks old. The results are illustrated in FIG. 12.

Figure 12:
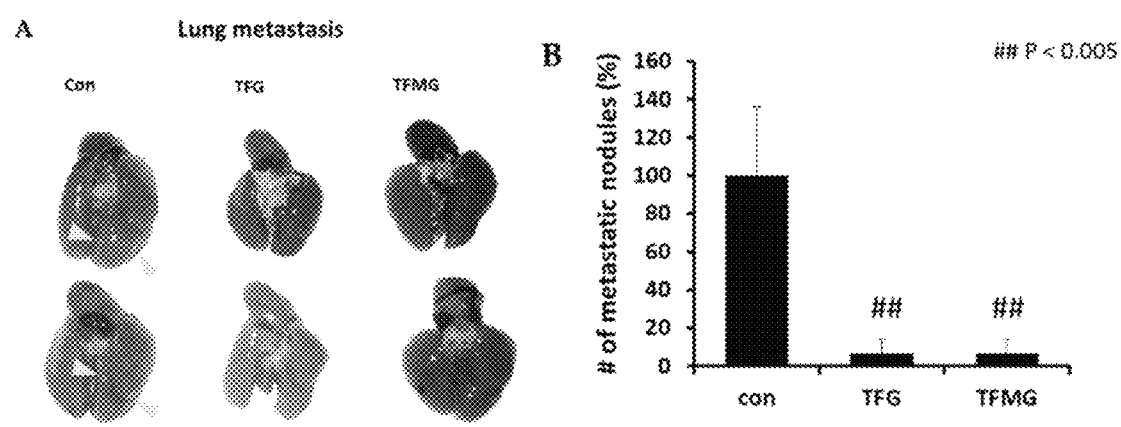
FIG. 12 is a view illustrating the results confirming the effects of the TFG nanoparticles or TFMG nanoparticles according to an example of the present invention on the inhibition of metastasis in a naturally occurring tumor model.

As illustrated in FIG. 12, it was confirmed that both experimental groups to which the TFG nanoparticles or TFMG nanoparticles were administered exhibited a metastasis inhibition rate of 93.6% as compared to the control. From the result, it could be confirmed that the TFG nanoparticles or TFMG nanoparticles also exhibited effects of inhibiting the metastasis of a tumor in the naturally occurring tumor model.

5.3. Confirmation of Normalization Effects of Blood Vessels

Figure 13:
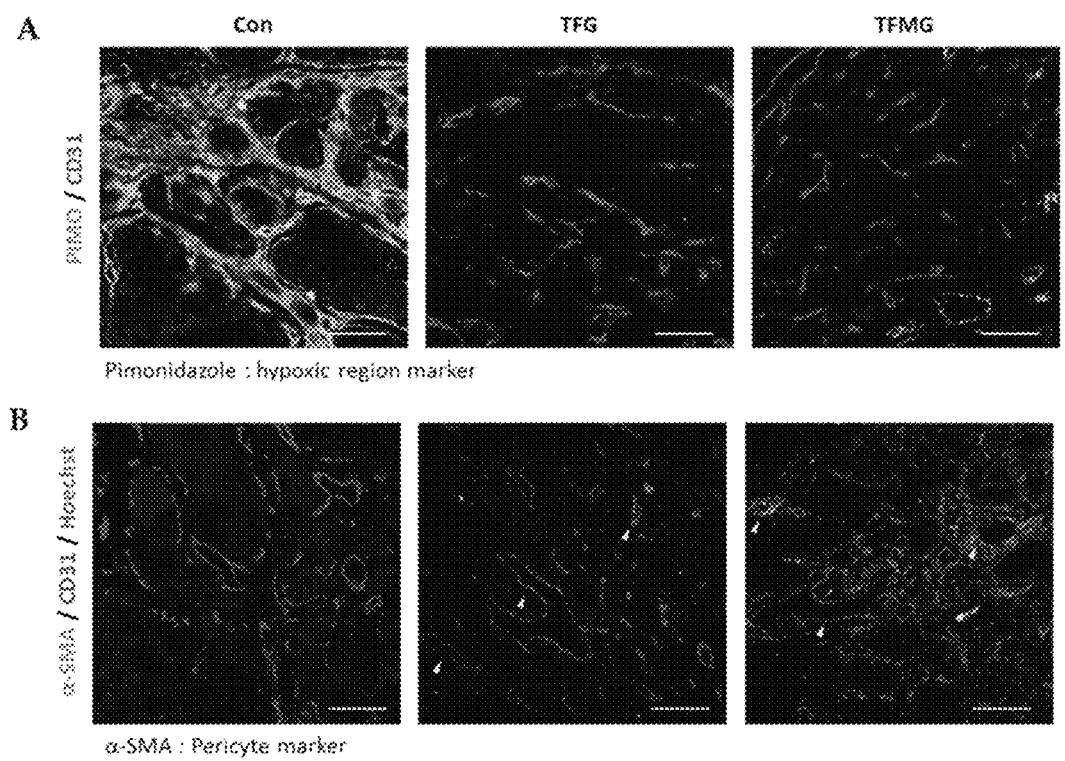
FIG. 13 is a view illustrating the results confirming the effects of the TFG nanoparticles or TFMG nanoparticles according to an example of the present invention on the normalization of blood vessels in a naturally occurring tumor model.

In order to confirm whether normalization effects of blood vessels in a tumor are also exhibited in the naturally occurring tumor model, it was confirmed that 100 nM of the TFG nanoparticles or TFMG nanoparticles was injected into the tail veins of 12-week-old WTV-PyMT gene transplanted mice, and the normalization effects of blood vessels were confirmed in the same manner as in Example 3 when the mice became 15 weeks old. The results are illustrated in FIG. 13.

As illustrated in FIG. 13A, it was confirmed that the hypoxic state observed inside the tumor was remarkably decreased in the experimental groups to which the nanoparticles were administered. Further, as illustrated in FIG. 13B, it could be confirmed that endothelial cells were increased. From the results, it could be confirmed that the TFG nanoparticles or TFMG nanoparticles normalized abnormal blood vessels in a tumor.

According to the results, the TFG nanoparticles or TFMG nanoparticles of the present invention may inhibit the proliferation and/or metastasis of solid cancer cells by weakening the hypoxic conditions of blood vessels inside solid cancer and normalizing abnormal blood vessels, and may remarkably increase the treatment efficacy of a conventionally used anticancer agent by normalizing blood vessels inside solid cancer, showing that the TFG nanoparticles or TFMG nanoparticles of the present invention may be used alone for the treatment of solid cancer, and may be used together with the existing anticancer agent to remarkably increase the treatment efficiency of cancer.

The above-described description of the present invention is provided for illustrative purposes, and those skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

Since the TFG nanoparticles or TFMG nanoparticles according to the present invention can not only inhibit the proliferation, metastasis, recurrence, and the like of cancer cells alone, but can also significantly increase the treatment efficiency of various cancer treatment therapies that are conventionally used by aggravating hypoxic conditions inside cancer tissues and promoting the generation of endothelial cells, it is expected that the TFG nanoparticles or TFMG nanoparticles according to the present invention can be effectively used for various cancer treatments. In addition, it is expected that the TFG nanoparticles or TFMG nanoparticles according to the present invention can also be used in treatment adjuvant therapy for diseases with excessive vasculogenesis/angiogenesis.

INDUSTRIAL APPLICABILITY

Since nanoparticles including the amino acid sequence represented by SEQ ID NO: 1 of the present invention or nanoparticles including the amino acid sequence represented by SEQ ID NO: 2 of the present invention may directly treat cancer, inhibit the metastasis of cancer, and remarkably improve the treatment effects of anticancer therapy by normalizing blood vessels inside cancer tissues, it is expected that the nanoparticles will be effectively used for the treatment of various cancers.

What is claimed is:

1. A method for treating cancer, comprising a step of administering, to an individual having lung cancer, a composition comprising, as an active ingredient, nanoparticles comprising an amino acid sequence represented by SEQ ID NO: 1 or nanoparticles comprising an amino acid sequence represented by SEQ ID NO: 2, wherein the composition normalizes blood vessels inside cancer tissues by alleviating hypoxic conditions and increasing pericytes in cancer tissues.

2. The method of claim 1, wherein the composition inhibits the proliferation, metastasis, and recurrence of cancer or resistance to anticancer therapy.

3. The method of claim 1, wherein the individual is a patient undergoing anticancer therapy.

4. The method of claim 3, wherein the anticancer therapy is radiation therapy or anticancer agent therapy.

5. A method for treating cancer, comprising a step of administering, to an individual having lung cancer, a composition comprising an anticancer agent and, as an active ingredient, nanoparticles comprising an amino acid sequence represented by SEQ ID NO: 1 or nanoparticles comprising an amino acid sequence represented by SEQ ID NO: 2, wherein the composition improves treatment effects of an anticancer agent through normalization of blood vessels inside cancer tissues by alleviating hypoxic conditions and increasing pericytes in cancer tissues.

6. A method for inhibiting the metastasis of lung cancer, comprising a step of administering, to an individual, a composition comprising, as an active ingredient, nanoparticles comprising an amino acid sequence represented by SEQ ID NO: 1 or nanoparticles comprising an amino acid sequence represented by SEQ ID NO: 2, wherein the composition normalizes blood vessels inside cancer tissues by alleviating hypoxic conditions and increasing pericytes in cancer tissues.

7. The method of claim 6, wherein the metastasis is metastasis into the lungs or the lymph nodes.

8. A method of alleviating hypoxic conditions and increasing pericytes in cancer tissues of an individual having lung cancer, comprising administering a composition to the individual, wherein the composition comprises nanoparticles comprising an amino acid sequence represented by SEQ ID NO: 1 or nanoparticles comprising an amino acid sequence represented by SEQ ID NO: 2.

* * * * *

SEQUENCE LISTING

```
<160> NUMBER OF SEQ ID NOS: 2

<210> SEQ ID NO 1
<211> LENGTH: 237
<212> TYPE: PRT
<213> ORGANISM: Artificial Sequence
<220> FEATURE:
<223> OTHER INFORMATION: TFG nanoparticle

<400> SEQUENCE: 1

Met Gly Gly Thr Thr Phe Leu Leu Arg Asn Ala Ser Gly His Met Ser
1               5                   10                  15

Ser Gln Ile Arg Gln Asn Tyr Ser Thr Asp Val Glu Ala Ala Val Asn
            20                  25                  30

Ser Leu Val Asn Leu Tyr Leu Gln Ala Ser Tyr Thr Tyr Leu Ser Leu
        35                  40                  45

Gly Phe Tyr Phe Asp Arg Asp Asp Val Ala Leu Glu Gly Val Ser His
    50                  55                  60

Phe Phe Arg Glu Leu Ala Glu Glu Lys Arg Glu Gly Tyr Glu Arg Leu
65                  70                  75                  80

Leu Lys Met Gln Asn Gln Arg Gly Gly Arg Ile Phe Leu Gln Asp Ile
                85                  90                  95

Lys Lys Pro Ala Glu Asp Glu Trp Gly Lys Thr Pro Asp Ala Met Lys
            100                 105                 110

Ala Ala Met Ala Leu Glu Lys Lys Leu Asn Gln Ala Leu Leu Asp Leu
        115                 120                 125
```

```
His Ala Leu Gly Ser Ala Arg Thr Asp Pro His Leu Cys Asp Phe Leu
            130                 135                 140

Glu Thr His Phe Leu Asp Glu Val Lys Leu Ile Lys Lys Met Gly
145                 150                 155                 160

Asp His Leu Thr Asn Leu His Arg Leu Gly Gly Ser Glu Phe Val
                165                 170                 175

Asp Gly Gly Gly Ser Gly Thr Ser Ala Asn Ser Phe Leu Glu Glu Leu
                180                 185                 190

Arg His Ser Ser Leu Glu Arg Glu Cys Ile Glu Ile Cys Asp Phe
                195                 200                 205

Glu Glu Ala Lys Glu Ile Phe Gln Asn Val Asp Thr Leu Ala Phe
210                 215                 220

Trp Ser Lys His Val Leu Glu His His His His His His
225                 230                 235
```

<210> SEQ ID NO 2
<211> LENGTH: 244
<212> TYPE: PRT
<213> ORGANISM: Artificial Sequence
<220> FEATURE:
<223> OTHER INFORMATION: TFMG nanoparticle

<400> SEQUENCE: 2

```
Met Gly Gly Thr Thr Phe Leu Leu Arg Asn Ala Ser Gly His Met Ser
1               5                   10                  15

Ser Gln Ile Arg Gln Asn Tyr Ser Thr Asp Val Glu Ala Ala Val Asn
                20                  25                  30

Ser Leu Val Asn Leu Tyr Leu Gln Ala Ser Tyr Thr Tyr Leu Ser Leu
            35                  40                  45

Gly Phe Tyr Phe Asp Arg Asp Asp Val Ala Leu Glu Gly Val Ser His
        50                  55                  60

Phe Phe Arg Glu Leu Ala Glu Glu Lys Arg Glu Gly Tyr Glu Arg Leu
65                  70                  75                  80

Leu Lys Met Gln Asn Gln Arg Gly Gly Arg Ile Phe Leu Gln Asp Ile
                85                  90                  95

Lys Lys Pro Ala Glu Asp Glu Trp Gly Lys Thr Pro Ala Met Lys
            100                 105                 110

Ala Ala Met Ala Leu Glu Lys Lys Leu Asn Gln Ala Leu Leu Asp Leu
            115                 120                 125

His Ala Leu Gly Ser Ala Arg Thr Asp Pro His Leu Cys Asp Phe Leu
            130                 135                 140

Glu Thr His Phe Leu Asp Glu Val Lys Leu Ile Lys Lys Met Gly
145                 150                 155                 160

Asp His Leu Thr Asn Leu His Arg Leu Gly Gly Ser Glu Phe Val
                165                 170                 175

Asp Gly Gly Gly Ser Gly Thr Ser Gly Pro Leu Gly Leu Ala Gly Ala
                180                 185                 190

Asn Ser Phe Leu Glu Glu Leu Arg His Ser Ser Leu Glu Arg Glu Cys
            195                 200                 205

Ile Glu Glu Ile Cys Asp Phe Glu Glu Ala Lys Glu Ile Phe Gln Asn
        210                 215                 220

Val Asp Asp Thr Leu Ala Phe Trp Ser Lys His Val Leu Glu His His
225                 230                 235                 240

His His His His
```